United States Patent [19]

Bellgrau et al.

[11] Patent Number: 5,759,536
[45] Date of Patent: Jun. 2, 1998

[54] USE OF FAS LIGAND TO SUPRESS T-LYMPHOCYTE-MEDIATED IMMUNE RESPONSES

[75] Inventors: Donald Bellgrau; Richard C. Duke, both of Denver, Colo.

[73] Assignee: University Technology Corporation, Boulder, Colo.

[21] Appl. No.: 378,507

[22] Filed: Jan. 26, 1995

Related U.S. Application Data

[63] Continuation-in-part of Ser. No. 250,478, May 27, 1994, abandoned.

[51] Int. Cl.$^6$ .......................... A01N 48/00; A01N 63/00; A01N 65/00
[52] U.S. Cl. .................. 424/93.21; 424/93.1; 424/93.2; 424/93.3; 424/93.7; 935/59; 935/62
[58] Field of Search ........................ 424/93.1, 93.2, 424/93.21, 93.3, 93.7; 435/172.3; 800/2, DIG. 1; 935/59, 62

[56] References Cited

U.S. PATENT DOCUMENTS

| | | |
|---|---|---|
| 5,219,740 | 6/1993 | Miller et al. |
| 5,283,058 | 2/1994 | Faustman .................................. 424/88 |

OTHER PUBLICATIONS

S Nagata et al (1995) Science 267:1449–1456.
LB Owen–Schaub et al (1992) Cellular Immunology 140: 197–205.
R Jaenisch (1988) Science 240: 1468–1474.
MD Walker et al (1983) Nature 306: 557–561.
JD Watson et al (1987) Molecular Biology of the Gene, p. 313.
Naji et al., "The Influence of Histocompatibility and Transplant Site on Parathyroid Allograft Survival," *J. Surgical Research* (1976) 20:261–267.
Naji et al., Spontaneously Diabetes in Rats: Destruction of Islets Is Prevented by Immunological Tolerance, *Science* (1981) 213:1390–1392.
Selawry et al., "Intratesticular Islet Allografts in the Spontaneous Diabetic BB/W Rat," *Diabetes* (1985) 34:1019–1024.

Bellgrau and Selawry, "Cyclosporine–induced Tolerance to Intratesticular Islet Xenografts," *Transplantation* (1990) 50:654–657.
London et al., "A Simple Method for the Release of islets by Controlled Collagenase Digestion of the Human Pancreas," *Transplantation* (1990) 49:1109–1113.
Selawry et al., "Production of a Factor, or Factors, Suppressing IL–2 Production and T Cell Proliferation by Sertoli Cell–enriched Preparations," *Transplantation* (1991) 52:846–850.
Suda et al., "Molecular Cloning and Expression of the Fas Ligand, a Novel Member of the Tumor Necrosis Factor Family" *Cell* (1993) 75:1169–1178.
Selawry and Cameron, "Sertoli Cell–enriched Fractions in Successful Islet Cell Transplantation," *Cell Transplantation* (1993) 2:123–129.
Suda and Nagata, "Purification and Characterization of the Fas–ligand that Induces Apoptosis," *J. Exp. Med.* (1994) 179:873–879.
Selawry et al., "Extended Survival of MHC–Compatible Islet Grafts From Diabetes–Resistant Donors in Spontaneously Diabetic BB/W Rat," *Diabetes* (1987) 36:1061–1067.
Johnstone & Thorpe, "Immunochemistry in Practice", by Blackwell Scientific Publications, Oxford, (1987) pp. 30–47.
Lee et al., "Fas Ligand Expression on an Activated Cytotoxic T–cell Line", FASEB J. (1994) 8:A770.
Takahashi et al., "Generalized Lymphoproliferative Disease in Mice, Caused by a Point Mutation in the Fas Ligand", *Cell* (1994) 76:969–976.
Takahashi et al., "Human Fas ligand:gene structure, chromosomal location and species specificity", *International Immunology* (1994( 6:1567–1574.

*Primary Examiner*—Bruce R. Campbell
*Attorney, Agent, or Firm*—Sheridan & Ross, P.C.

[57] ABSTRACT

A method for inhibiting T-lymphocyte-mediated immune responses, including those directed against autologous and/or heterologous tissues, e.g., by a recipient mammal of a transplanted tissue, said method comprising providing the recipient mammal with Fas ligand. The Fas ligand may be provided to the recipient mammal by a variety of means, including by pump implantation or by transplantation of transgenic tissue expressing Fas ligand. Also provided is a method for diagnostic use of Fas ligand expression in improving transplantation success.

7 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
- ( A ) LENGTH: 20 nucleotides
- ( B ) TYPE: nucleic acid
- ( C ) STRANDEDNESS: single
- ( D ) TOPOLOGY: linear ( x i ) SEQUENCE DESCRIPTION: SEQ ID NO:1:

GCCCGTGAAT TACCCATGTC                    20

( 2 ) INFORMATION FOR SEQ ID NO:2:

( i ) SEQUENCE CHARACTERISTICS:
- ( A ) LENGTH: 20 nucleotides
- ( B ) TYPE: nucleic acid
- ( C ) STRANDEDNESS: single
- ( D ) TOPOLOGY: linear ( x i ) SEQUENCE DESCRIPTION: SEQ ID NO:2:

TGGTCAGCAA CGGTAAGATT                    20

( 2 ) INFORMATION FOR SEQ ID NO:3:

( i ) SEQUENCE CHARACTERISTICS:
- ( A ) LENGTH: 19 nucleotides
- ( B ) TYPE: nucleic acid
- ( C ) STRANDEDNESS: single
- ( D ) TOPOLOGY: linear ( x i ) SEQUENCE DESCRIPTION: SEQ ID NO:3:

AACATAGAGC TGTGGCACC                     19

USE OF FAS LIGAND TO SUPRESS T-LYMPHOCYTE-MEDIATED IMMUNE RESPONSES

CROSS REFERENCE TO RELATED APPLICATIONS

This application is a continuation-in-part of earlier filed application Ser. No. 08/250,478, filed May 27, 1994, abandoned, which application is incorporated herein by reference and to which application is claimed priority under 35 USC § 120.

BACKGROUND OF THE INVENTION

This invention relates to suppression of T-lymphocyte-mediated immune responses, including those directed against autologous tissue in autoimmune conditions and/or transplanted tissues, e.g., rejection of autologous tissue in autoimmune conditions or of allogeneic or xenogeneic tissue transplanted into patients in need of such tissues, e.g., transplants of porcine islet cells into patients who have or are at risk of developing diabetes mellitus.

Type I or juvenile onset diabetes is a major health problem in the United States. Diabetes and its complications double the risk of fatal heart disease and increase the risk of blindness and stroke at least four fold. Diabetes mellitus is characterized by insulin deficiency which prevents normal regulation of blood glucose levels, and which leads to hyperglycemia and ketoacidosis. The primary cause of kidney failure leading to kidney transplantation is diabetes.

Insulin, a peptide hormone, promotes glucose utilization, protein synthesis, formation and storage of neutral lipids, and the growth of some cell types. Insulin is produced by the β cells within the islets of Langerhans of the pancreas. Early-onset diabetes (10–20% of cases) is caused by an auto-immune reaction that causes complete destruction of β cells. Adult-onset diabetes has a number of causes, but in most cases the β islet cells are defective in secretion of insulin.

Insulin injection therapy, usually with porcine or bovine insulin, prevents severe hyperglycemia and ketoacidosis, but fails to completely normalize blood glucose levels. While injection therapy has been quite successful, it fails to prevent the premature vascular deterioration that is now the leading cause of morbidity among diabetics. Diabetes-related vascular deterioration, which includes both microvascular degeneration and acceleration of atherosclerosis, can eventually cause renal failure, retinal deterioration, angina pectoris, myocardial infarction, peripheral neuropathy, and arteriosclerosis.

Large scale production of human insulin has become possible with the cloning of the human insulin gene, which has begun to replace bovine and porcine insulin as the treatment of choice. Use of human insulin has eliminated some of the problems associated with other forms of insulin, including antibody-mediated insulin resistance and allergic reactions resulting from the slightly different structures of non-human insulins. Despite these advantages, treatment with human insulin does not prevent vascular deterioration.

Insulin delivery pumps have been developed which administer varying doses of insulin based on activity, diet, time of day, and other pre-programmed factors. While such devices improve blood sugar control, they also do not prevent vascular deterioration.

While the maintenance of blood sugar control with exogenous insulin has proved of significant value in reducing diabetes-related complications, the most effective form of therapy is thought to be providing patients with an endogenous source of insulin. Surgical transplantation of part or all of the pancreas is difficult, however, because the pancreas is a fragile and complicated organ, the only practical source is a deceased donor. Further, only a small portion of the pancreas, the β cells of the islet of Langerhans, produce insulin; the remainder of the pancreas presents a potent target for transplant rejection. Transplantation of just the islets of Langerhans is a desirable goal, as they continue to secrete appropriate amounts of insulin in response to nutritional signals even when isolated from the rest of the pancreas.

Islet cell transplantation has been successfully performed in animals made diabetic by prior treatment with a drug which destroys β cells. Successful transplantation in these animals has been shown to restore normal blood glucose regulation and reduce further vascular deterioration. In these animal models, it is possible to use islet cells from donors which are syngeneic (fully tissue compatible, also referred to as histocompatible) to the diabetic recipient. In humans, fully tissue compatible donors are rare (1 in 200,000) and so from a practical standpoint, islets from mismatched humans (allografts) or non-humans (xenografts) will need to be employed.

A major problem associated with transplantation of any tissue is immune-mediated graft rejection in which the recipient's T-lymphocytes recognize donor histocompatibility antigens as foreign. Thus, even though human and xenogeneic insulin can be used to partially control diabetes, the use of allografts and/or xenografts as a true therapy for diabetes depends on preventing transplant rejection. Current regimes for transplanting many tissues and organs require life-long administration of immunosuppressive drugs. These drugs have serious side-effects and can cause increased susceptibility to infection, renal failure, hypertension, and tumor development.

In addition to transplant rejection based on recognition of allogeneic and xenogeneic tissue differences, it has been observed first in diabetic rodents and later in humans that transplanted islet cells could be destroyed in diabetic hosts even when host and donor were genetically identical. Naji et al. (1981) Science 213:1390 showed that spontaneously diabetic animals maintained a skin and bone marrow allograft while an islet allograft of the same genetic makeup as the skin and bone marrow allograft was destroyed. It appears that the disease process that destroyed the native islet β cells can recur and destroy transplanted islet cells. This phenomenon, termed disease recurrence, is the process in which a target tissue is destroyed independent of histocompatibility differences between donor and host that are involved in allograft responses. This disease differs from conventional transplantation responses in several ways. Perhaps the most important difference is that the dose of immunosuppression which can be effectively used to prevent acute rejection of most allografts (e.g., kidney, liver, etc.) is not nearly as effective in preventing disease recurrence in diabetes. This lack of effectiveness is equally true for xenografts. Increasing the dose of immunosuppression leads to toxicity. Thus, it is clear that approaches must be developed which protect transplanted cells against both transplant rejection and disease recurrence.

A second problem has been the paucity of islet tissue suitable for transplantation. While sources of donor insulin from non-primate species is clinically effective in reversing hyperglycemia, xenogeneic donor tissue is subject to violent rejection. Further, the ready accessibility of non-human donors as a source of islet tissue has been to date of no practical value.

Several immunologically privileged sites in mammals allow prolonged survival of transplanted allografts (Naji & Barker (1976) J. Surg. Res. 20:261–267). The remarkable survival of islet allo- and xenografts transplanted into abdominal testes has been reported (Selawry & Fojaco (1985) Diabetes 34:1019–1024; Bellgrau & Selawry (1990) Transplantation 50:654–657; Selawry et al. (1987) Diabetes 36:1061–1067). Selawry et al. (1991) Transplantation 52:846–850 have shown that an unknown factor or factors released by testicular Sertoli cells appears to be responsible for the protection of the intratesticular islet allo- and xenografts against rejection. This unknown factor (s) has been reported to inhibit the production of IL-2 in vitro (Selawry et al. (1991) supra).

Selawry & Cameron (1993) Cell Transplantation 2:123–129 studied the use of Sertoli cells to establish an immunologically privileged site in vivo in the renal subcapsular space. Diabetic PVG rats received rat islet cells grafts with and without Sertoli cells (Sertoli enriched fraction, or SEF) and with and without cyclosporine (CsA). The results showed that 70%–100% of the recipient rats receiving islet cells alone, islet cells and CsA alone, or islet cells and SEF alone, remained hyperglycemic. In contrast, prolonged normoglycemia in excess of 100 days was achieved in rats receiving a combination of islet cells, SEF, and CsA.

SUMMARY OF THE INVENTION

This invention is based in part on the discovery by the inventors that the factor released by testicular Sertoli cells responsible for the protection of the intratesticular islet allo- and xenografts against rejection is the Fas ligand.

Accordingly, the invention features a method for suppressing T-lymphocyte-mediated rejection by a recipient mammal of transplanted tissue by administering to the recipient mammal an effective amount of the Fas ligand. The donor mammal may be the same or a different species as the recipient mammal.

In another aspect, the invention also features a method for suppressing and preventing T-lymphocyte-mediated disease recurrence, such as recurrence of diabetic disease, by administering to the patient in need thereof an effective amount of the Fas ligand.

In another aspect, the invention also features a method for treating T-lymphocyte-mediated primary disease, such as juvenile diabetes, by administering to the patient an effective amount of the Fas ligand.

The invention further features a method for suppressing T-lymphocyte-mediated rejection by a recipient mammal of transplanted tissue by introducing into the recipient mammal a cell which expresses the Fas ligand.

The invention also features a method for suppressing and preventing T-lymphocyte-mediated disease recurrence, such as recurrence of diabetic disease, by introducing into a mammal in need thereof a cell which expresses the Fas ligand.

This invention also features a method for treating T-lymphocyte-mediated primary disease, such as juvenile diabetes, by introducing into a mammal in need thereof a cell which expresses the Fas ligand.

The invention also features a transgenic non-human animal containing a DNA sequence encoding the Fas ligand in its germ and somatic cells. The transgenic non-human animal of the invention is capable of expressing biologically active Fas ligand in cells of all organs and tissues, and is thus useful as a source of donor organs or cells which, because they express the Fas ligand, will be less susceptible to rejection.

In one embodiment of the Fas ligand administration of the invention, purified natural or recombinant Fas ligand is provided to the recipient mammal at the site of the transplant graft. In another embodiment of the invention, the transplanted tissue itself functions as a source of Fas ligand. In this embodiment, transplanted tissue is obtained from a non-human animal which contains the gene encoding the Fas ligand in its germ and somatic cells. The transgenic tissue containing the Fas ligand gene maintains its ability to express biologically active Fas ligand when transplanted into the recipient host animal. The invention includes the transplant of Fas ligand-expressing tissue alone, e.g., transplant of transgenic islet cells into a diabetic patient, or transplantation of Fas ligand-expressing autologous tissue along with non-manipulated donor tissue, e.g., transplant of non-transgenic islet cells to a patient in need thereof with Fas ligand-expressing tissue to the graft site, thereby creating an artificial immunologically-privileged site. In this case, the transplanted Fas ligand-expressing tissue functions to suppress rejection of the transplanted islet cells.

Other features and advantages of the invention will be apparent from the following description of the preferred embodiments thereof, and from the claims.

DETAILED DESCRIPTION

Reference will now be made in detail to useful embodiments of the invention, which, together with the following examples and claims, serve to explain the principles of the invention. It is to be understood that this invention is not limited to the specific examples described, and as such may, of course, vary. It is also to be understood that the terminology used herein is with the purpose of describing particular embodiments only, and is not intended to limit the scope of the invention which will be limited only by the appended claims.

Unless defined otherwise, all technical and scientific terms used herein have the same meaning as commonly understood by one of ordinary skill in the art to which this invention belongs. Although any methods and materials similar to or equivalent to those described herein can be used in the practice or testing of the invention, the preferred methods and materials are now described. All publications mentioned herein are incorporated herein by reference to describe and disclose specific information for which the reference was cited in connection with.

The Fas ligand, which is the naturally occurring ligand of Fas, was recently purified and identified as a 40 kd membrane glycoprotein (Suda et al. (1993) Cell 75:1169–1178). The purified Fas ligand exhibits cytolytic activity against cells expressing Fas.

The Fas ligand is used, according to the invention, to suppress T-lymphocyte-mediated rejection of transplanted tissue. The Fas ligand is also used to prevent T-lymphocyte-mediated disease recurrence, and to treat T-lymphocyte-mediated primary disease. The methods of the invention involve providing an amount of Fas ligand effective to suppress T-lymphocyte-mediated rejection of transplanted tissue, disease recurrence, and/or primary disease.

In activation of the immune system, lymphocytes are presented with a foreign antigen. The lymphocytes respond by differentiating into effector cells, and the effector cells then clear the foreign antigen. In rejection of an allograft, the immune system of the recipient animal has not previously been primed to respond because the immune system for the most part is only primed by environmental antigens. Tissues from other members of the same species have not been presented in the same way that, for example viruses and bacteria have been presented. In the case of allograft rejection, immunosuppressive regimens are designed to prevent the immune system from reaching the effector stage. However, the immune profile of xenograft rejection may resemble disease recurrence more than allograft rejection. In the case of disease recurrence, the immune system has already been activated, as evidenced by destruction of the native islet cells. Therefore, in disease recurrence the immune system is already at the effector stage. The Fas ligand is able to suppress the immune response to both allografts and xenografts because lymphocytes activated and differentiated into effector cells express Fas, and thereby are susceptible to the Fas ligand.

A reaction or disease is considered to be T-lymphocyte-mediated when T-lymphocytes are required in mediating the reaction or disease effect. Where cells of the tissue for transplantation (the "donor" tissue) bear on their surfaces foreign histocompatibility antigens, these antigens cause cytotoxic T-lymphocyte activation in recipients, terminating in donor cell destruction after several sequential activation steps. The cascade is initiated by conjugate formation between the antigen-specific T-cell receptor on host T-lymphocytes and the major histocompatibility antigens on the donor cell. Conjugate formation is followed by T-lymphocyte-mediated activation, resulting in donor cell death. This process can eventually result in rejection even in intra-species transplantation. According to the invention, this problem is addressed by suppressing the T-lymphocyte response prior to the stage where donor cell destruction is initiated.

While the invention specifically addresses transplant rejection and disease recurrence, the invention is useful for inhibiting other types of T-lymphocyte-mediated medical conditions. Lymphocytes activated by disease as well as by the introduction of foreign grafts express Fas, and therefore, are susceptible to treatment with Fas ligand. In general terms, the Fas ligand as an immunosuppressive agent is most active against a primed or activated immune system. The primed or activated immune system may be associated with disease conditions in which either T-lymphocytes or B-lymphocytes are activated. Activated T-lymphocytes are associated with disease in graft versus host reactions (e.g., bone marrow transplantation) and most forms of autoimmunity, including but not restricted to, multiple sclerosis, rheumatoid arthritis, lupus, and myasthenia gravis. Fas expressing leukemia may also be susceptible to treatment with the Fas ligand, since Fas is expressed by B- and T-lymphocyte tumors.

The Fas ligand may be used to treat chronic transplant rejection. It is recognized by the art that most transplants undergo a chronic graft destructive process. The mechanism of chronic transplant rejection differs from conventional allograft immunity and conventional immunosuppression has been ineffective in its treatment. Chronic graft rejection may be treated with the Fas ligand, resulting in successful engraftment for longer periods of time and allowing donor tissue to be used for new recipients.

The Fas ligand may also be used to treat acute graft rejection. Often a transplant recipient host goes through a crisis period where the transplant undergoes a severe graft rejection which cannot be resolved with the immunotherapy (usually cyclosporine) that may prevent the immune system from reaching the effector phase but is not effective against activated effector cells. A conventional route of therapy for acute graft rejection is the use of antibody to the T-lymphocyte receptor complex. This results in severe immunosuppression in the recipient host. Treatment with the Fas ligand should provide a more specific treatment for activated cells, that is, for cells attacking the transplant tissue, not all the T-lymphocytes present in the immune system.

There is in the art recognized need for a safe and effective new form of immunosuppressive agent—one that would resist the attacks of the immune response in disease recurrence as well as the violent immune response to xenogeneic donor tissue. This invention addresses that need by providing methods which allow the use of non-human tissue for transplantation into a human patient in need thereof. The method of the invention prevents rejection of xenogeneic tissue. The invention thus permits not just intra-species transplantation of tissues and organs, but xenografts as well, opening up the possibility of "farming" of donor organs and tissues in non-human mammals for transplantation into human patients. In the case of xenografts, this invention may be practiced along with other methods for masking, modifying, or eliminating undesirable antigens on the surface of donor cells, such as the method described in U.S. Pat. No. 5,283,058, herein incorporated by reference.

By "endogenous source of Fas ligand" is meant providing means by which the Fas ligand is synthesized and secreted within the host recipient mammal itself. In contrast, an exogenous source of Fas ligand may be provided by continuous infusion of purified Fas ligand through a pump implanted into the host recipient mammal.

Donor Tissue. Donor tissue may be obtained from the same or a different species as the recipient mammal. The term "donor tissue" includes cells and organs from a donor mammal, including but not limited to islet cells, kidney, heart, liver, lung, brain, and muscle tissue.

The donor tissue may be obtained from any mammal, preferably pigs. Pigs offer many advantages for use as organ and cell donor animals. For example, many porcine organs, such as the heart and kidney, are of a similar size to human organs.

Purified Fas Ligand. The Fas ligand administered may be obtained from naturally occurring sources, and may be purified from any animal or cell source, including mouse, rat, pig, etc. A simple method for purifying Fas ligand from cultured PC60-d10S cells is described by Suda & Nagata (1994) supra.

The invention also contemplates use of purified Fas ligand produced by recombinant DNA technology. The recombinant methods necessary to produce high quantities of Fas ligand of high purity are known to the art. For example, recombinant mouse Fas ligand has been produced by Suda et al. (1993)supra. Recombinant Fas ligand may originate from any suitable source, including human Fas ligand. Example 1 describes production of recombinant human Fas ligand.

Administration of Fas ligand. Purified Fas ligand is administered to a transplant recipient to suppress T-lymphocyte-mediated rejection of the transplanted tissue by the recipient mammal and to suppress recurrence of a disease which destroyed the endogenous tissue being replaced.

Purified Fas ligand may be administered by a number of methods known in the art. In one embodiment of the invention, a therapeutic or pharmaceutical composition comprising Fas ligand is administered in an effective amount to a mammal sufficient to prevent a T-lymphocyte-mediated transplant rejection or disease recurrence. The therapeutic or pharmaceutical composition of the invention may be administered in a variety of ways, including by injection or by continuous infusion from an implanted pump. Other appropriate administration forms are envisioned. For example, semipermeable implantable membrane devices that are useful as means for delivering drugs or medications are known. The encapsulation of cells that secrete neurotransmitter factors, and the implantation of such devices into the brain of patients suffering from Parkinson's disease has been described. See, U.S. Pat No. 4,892,538; U.S. Pat. No. 5,011,472; U.S. Pat. No. 5,106,627. Formulations of purified Fas ligand may contain one or more agents and excipients.

In one embodiment of the invention, Fas ligand is therapeutically administered by implanting into patients, transfected cells capable of expressing and secreting a biologically-active form of Fas ligand.

Example 1 describes the transplantation of rat islet cells into the renal subcapsular space of diabetic PVG rats. Pumps dispensing saline (controls) or purified Fas ligand (experimentals) are implanted in proximity to the graft site.

An alternative to administration of purified Fas ligand to the graft site, transplant tissue can be grown in transgenic animals which have been genetically altered to contain the Fas ligand gene sequence. Such transgenic animals can be made by standard transgenic techniques (Example 2). Example 3 describes transplantation of islet cells from transgenic rats wherein the transplanted tissue itself is an endogenous source of Fas ligand.

The invention may be used to treat a number of human disease conditions resulting from destruction of endogenous cells, such as the destruction of insulin producing pancreatic islet β cells in diabetes. An important feature of the invention is that it makes possible use of non-human mammals as tissue and organ donors for human patients. The above methods describe the use of the invention to treat diabetic human patients by transplantation of xenogeneic islet cells. The xenogeneic islet cells may be obtained from, for example, normal or transgenic pigs expressing the Fas ligand protein. Example 4 describes transplantation of transgenic porcine islet cells into a diabetic human patient.

The production of Fas ligand mRNA in Sertoli cells was established as described in Example 6. mRNA from purified rat Sertoli cells probed with a Fas ligand specific oligonucleotide showed that Sertoli cells are the primary if not exclusive source of the Fas ligand in testicular tissue. To test whether the absence of a functional Fas ligand molecule prohibited Sertoli cells from providing their immunosuppressive function, testicular tissue was transplanted a into Balb/c mice (Example 7). Both B6 and B6-Gld donors are genetically incompatible with the Balb/c recipients. The B6-Gld strain carries a point mutation in the Fas ligand gene preventing the expressed protein from functioning to engage apoptosis. While grafted B6 tissue remained healthy in the recipient Balb/c animals, the grafted B6-Gld tissue was completely destroyed within 7 days. These experiments were repeated with transplanted Sertoli cells isolated from B6 and B6-Gld animals into Balb/c recipients (Example 8). The results were identical to those obtained with transplanted tissue (Example 7).

EXAMPLE 1

Suppression of T-lymphocyte-Mediated Rejection of Transplanted Tissue by Administration of Fas Ligand Islet preparation. Freshly isolated islet cells from a rat are prepared according to known methods. See, for example, London et al. (1990) Transplantation 49:1109–1113. Under appropriate circumstances, islet cells may be pretreated prior to transplantation to conceal ("mask") donor antigens or modify graft immunogenicity by methods known in the art, for example, those described in U.S. Pat. No. 5,283,058.

Purified Fas ligand. Purified Fas ligand may be obtained from a mammalian source or produced in vitro as a recombinant protein. In one embodiment of the invention, purified Fas ligand is obtained from a naturally occurring source. A simple method for large scale purification of Fas ligand from cultured cells has been reported (Suda & Nagata (1994) supra). Briefly, cells expressing Fas ligand are cultured and harvested. A solubilized membrane fraction is purified by affinity purification, and the Fas ligand eluted as described by Suda & Nagata (1994) supra.

In another embodiment, Fas ligand is produced by recombinant DNA methods, utilizing the genes coding for Fas ligand. Expression of a recombinant rat Fas ligand has been obtained (Suda et al. (1993) Cell 75:1169–1178). The amino acid sequences of many proteins are highly conserved across a variety of mammalian species. As a consequence of the conservation of the nucleotide sequences there is considerable conservation of the nucleotide sequences of the genes that encode these proteins. Therefore, it is generally true that the gene encoding the Fas ligand in one mammalian species can cross-hybridize (i.e. form a stable double-stranded DNA hybrid) with the genes encoding that factor in other mammalian species under appropriate annealing conditions. This property may be used to identify cloned human DNA segments that include the gene for Fas ligand. For example, the human gene encoding the Fas ligand may be identified by screening a human genomic library using a $^{32}$P-labelled probe derived from the rat cDNA sequence of the Fas ligand (Suda et al. (1993) supra). Suitable host cells transformed with a vector containing DNA encoding the human Fas ligand are cultured under conditions for amplification of the vector and expression of the Fas ligand, and Fas ligand is harvested.

Bioassay of Fas ligand. The biological activity of purified Fas ligand is assessed in vitro with the cytotoxicity assay described by Suda & Nagata (1994) supra.

Transplantation of rats and administration of purified Fas ligand. Diabetic PVG rats are grafted with islet cells and implanted with pumps dispensing saline (controls) or purified Fas ligand (experimental) as follows. Diabetic PVG rats are anesthetized with methoxyflurane USP and the left flank opened to expose the kidney. Islets cells (10 islets/g of body weight) are injected under a renal capsule as described by Selawry & Cameron (1993) supra. A pump programmed to dispense either saline or purified Fas ligand over an empirically-determined period of time is implanted under the renal capsule. Cyclosporine (CsA) may be injected subcutaneously 25 mg/kg per day for a seven day period.

Recipient rats are evaluated for plasma glucose levels. Urine volumes and urine glucose contents are obtained and determined as described (Selawry & Cameron (1993) supra). Recipient rats receiving Fas ligand become normoglycemic over a prolonged period of time.

EXAMPLE 2

Production of Transgenic Mammals Containing DNA Encoding the Fas Ligand

A transgenic rat whose germ cells and somatic cells contain the Fas ligand gene is produced by methods known in the art. See, for example, U.S. Pat. No. 4,736,866 describing production of a transgenic mammal, herein incorporated by reference. Generally, the DNA sequence encoding the Fas ligand is introduced into the animal, or an ancestor of the animal, at an embryonic stage (preferably the one-cell, or fertilized oocyte, stage, and generally not later than about the 8-cell stage). There are several methods known to the art of introducing a foreign gene into an animal embryo to achieve stable expression of the foreign gene. One method is to transfect the embryo with the gene as it occurs naturally, and select transgenic animals in which the foreign gene has integrated into the chromosome at a locus which results in its expression. Other methods involve modifying the foreign gene or its control sequences prior to introduction into the embryo. For example, the Fas ligand gene may be modified with an enhanced, inducible, or tissue-specific promoter.

Tissues of transgenic rats are analyzed for the presence of Fas ligand, either by directly analyzing RNA, by assaying the tissue for Fas ligand, or by assaying conditioned medium for the secreted Fas ligand. For example, cells obtained from the transgenic rat are cultured in the presence of $^{35}$-methionine, the supernatant subjected to immunoprecipitation with antibodies to Fas ligand. Precipitated proteins are resolved by reducing SDS-polyacrylamide gel electrophoresis. and visualized by autoradiography. Conditioned medium may also be tested for in vitro cytotoxic activity by the method of Suda & Nagata (1994) supra.

EXAMPLE 3

Transplantation of Transgenic Islet Cells Expressing the Fas Ligand

Islet cells are obtained from the transgenic rat of Example 2 and grafted into diabetic PVG rats by the methods described in Example 1. Recipient rats. evaluated as described above. achieve normoglycemia for prolonged periods of time.

EXAMPLE 4

Transplantation of Transgenic Porcine Islet Cells into a Human Diabetic Patient

A transgenic pig is obtained all of whose germ cells and somatic cells contain a recombinant DNA sequence encoding human Fas ligand. The human Fas ligand DNA sequence was introduced into the pig by methods known to the art. Islet cells are obtained from the transgenic pig by the methods described in Example 2 and are grafted into diabetic human patient by methods known in the art. The human patient. evaluated appropriately, achieves normoglycemia for prolonged periods of time.

EXAMPLE 5

Other Embodiments

The method of the invention may also be used to prevent a recurring disease which resulted in destruction of endogenous tissue. For example. disease recurrence mediated by T-lymphocytes directed to islet β cell antigens results in destruction of grafted islet cells. Therefore, providing Fas ligand to the graft site prevents recurrence of diabetes and allows normoglycemia to be achieved in recipient mammals by suppressing the immune response directed to islet β cell antigens.

EXAMPLE 6

Production of Fas Ligand mRNA by Isolated Sertoli Cells cDNA synthesis. Total RNA from purified rat Sertoli cells was isolated from cell pellets by the method of Chomczynski and Sacchi (1987) Anal. Biochem. 162:156. The RNA (5 µg) was first denatured in methyl mercuric hydroxide (10 mM final concentration)(Alfa Products, Ward Hill. Mass.) and converted to cDNA in Taq (*Thermus aquaticus*) DNA polymerase buffer (50 mM KCl. 10 mM Tris-HCl. pH 8.3, 2.5 mM $MgCl_2$, and 0.01% gelatin) in the presence of RNA guard (20 units) (Pharmacia, Piscataway, N.J.), β-mercaptoethanol (40 mM), dNTPs (0.5 mM)(Pharmacia). 1 µg random hexamers (Pharmacia) and AMV (Avian myeloblastosis virus) reverse transcriptase (20 units) (Life Sciences Inc., St. Petersburg. Fla.) in a 50 µl reaction for 90 min at 42° C.

PCR amplification. Following synthesis, 5 µl of the cDNA was transferred to a tube on ice containing 200 mM dNTPs (Pharmacia). Taq polymerase buffer containing 1.5 mM $MgCl_2$, Taq DNA polymerase (1 unit)(Perkin Elmer Cetus, Norwalk, Conn.) and the rat Fas ligand specific oligonucleotide primers 5'-GCCCGTGAATTACCCATGTC-3' (SEQ ID NO:1) and 5'-TGGTCAGCAACGGTAAGATT-3' (SEQ ID NO:2) (forward and reverse, respectively). The samples were overlaid with light mineral oil (Sigma Chemical Corp., St. Louis. Mo.) and transferred to a thermal cycler (MJ Research. Inc., Watertown. Mass.). Following heating to 94° C. for 5 min to denature DNA/RNA complexes. the samples were amplified for 28 cycles of 1 min at 94° C., 1.5 min at 55° C., and 2 min at 72° C., followed by a final 10 min extension at 72° C.

Detection. 20 µl of the starting 50 µl reaction was separated by electrophoresis through a 1.6% agarose gel. The following samples were run: mRNA from Sertoli cells incubated at 32° C. (lane 1) or at 37° C. (lane 3); mRNA from Sertoli cells from a second animal incubated at 32° C. (lane 2) or at 37° C. (lane 4). The DNA in the gel was then transferred to nitrocellulose filters (Schleicher & Schuell, Keene, N.H.) according to the method of Southern (1975) J. Mol. Biol. 98:503. The filters were UV cross linked (Stratagene, San Diego, Calif.) and hybridized at 37° C. overnight in a solution containing 6X SSC (1X SSC=0.15M sodium chloride and 0.015M sodium citrate), 1X Denharts (0.02% each Ficoll 400, bovine serum albumin, and polyvinylpyrrolidone). 20 µg/ml wheat germ tRNA, 0.1% SDS and 0.05% sodium pyrophosphate plus the $^{32}$P end-labelled Fas ligand specific oligonucleotide 5'-AACATAGAGCTGTGGCACC-3' (SEQ ID NO:3). After extensive washing in 6X SSC plus 0.05% sodium pyrophosphate at 47° C., the filters were dried and exposed to Kodak X-Omat film.

An autoradiograph of the amplified rat Sertoli cell mRNA was obtained. Lanes 1 and 3 are mRNA from cells incubated at 32° C. or 37° C., respectively; lanes 2 and 4 are mRNA from Sertoli cells taken from a second animal cultured at 32° C. or 37° C., respectively. These results show that Sertoli cells are the dominant, if not exclusive, source of Fas ligand in the testis.

DNA sequencing. The PCR product was determined to be identical to that published by Suda et al. (1993) Cell 75:1169 by standard DNA sequencing methodology of Sanger et al. (1977) Proc. Natl. Acad. Sci. USA 78:5453.

EXAMPLE 7

Effect of Fas Ligand on Grafted Testicular Survival

To test whether the absence of a functional Fas ligand molecule prohibited Sertoli cells from providing their immunosuppressive function, we transplanted testicular tissue from male B6-Gld or genetically compatible but Fas ligand operative C57BL/6 (B6) mice into Balb/c recipients. The B6-Gld and B6 strains are identical at the major histocompatibility complex (MHC) and also share essentially all other (minor) histocompatibility antigens with the exception of the Fas ligand. B6-Gld carries a point mutation in the Fas ligand gene (Takahashi et al. (1994) Cell 7:969). B6-Gld and B6 differ from the Balb/c strain at both the MHC and multiple minor loci.

Testicular grafts of B6-Gld or B6 tissue were transplanted under the kidney capsule of Balb/c recipients. A mouse is weighed and injected with Avertin (12 ml/g), and anesthetized with Metophane. The mouse is shaved under the rib cage on the left side, and a small incision (about 8 mm) is made through the body wall. The adipose tissue attached to the posterior end of the kidney is pulled such that the kidney is externalized. The kidney is kept moist with Hank's Basic Salt Solution (HBSS). A straight incision is made on the posterior end of the kidney and the kidney capsule carefully loosened from the kidney with a probe. The tissue to be transplanted is deposited under the capsule and gently moved to the anterior part of the kidney with a probe. The kidney is replaced inside the body and the incision closed.

Blood Clot Transplantation Procedure. This procedure is designed to permit groups of cells or non-clustered islets to be transplanted under the recipient host kidney capsule. Embedding the cells within the clot allows the transplanter to place them in a relatively defined position from which they will not move.

Cells to be transplanted are transferred to a siliconized 15 ml centrifuge tube and allowed to settle for 5 min. Cells in a cell suspension are transferred to a siliconized 15 ml centrifuge tube and centrifuged at 300×g for 5 min. Most of the supernatant is removed and the cells resuspended in the remaining 200 μl medium. The cells are resuspended and transferred to a 300 μl microfuge tube, centrifuged at 500–1000×g for 30 sec and placed on ice. Most of the supernatant is removed, leaving about 4–5 mm fluid. With a scalpel, the top is cut just above the fluid level, and the remaining fluid removed with a capillary tube. Blood is drawn from the tail vein of the recipient animal and approximately 5 μl blood added to the cell pellet. A clot is allowed to form for 10 min. Residual sera is drawn off. The cells are embedded within the clot matrix and are not easily dislodged. The cell clot may then be transplanted into the kidney capsule.

Results. On days 2 and 7 (B6-Gld) or days 2, 7, and 28 (B6), the grafted tissue was analyzed macroscopically and microscopically for graft rejection. A recipient Balb/c mouse was euthanized with an overdose of penthrane. The kidney containing the graft was removed, fixed in a formal saline buffer solution and processed by routine histologic techniques. The kidney was embedded in paraffin after which 5 μl sections were cut and stained with hematoxylin and eosin. Renal tissue obtained from Balb/c kidney engrafted with B6 tissue appeared structurally normal by light microscopy. Transplanted tissue was observed adjacent to the kidney capsule. It appeared no different in morphology from that which was observed when histocompatible-genetically identical Balb/c tissue was used as the source of donor tissue. In B6-Gld engrafted kidney there was extensive infiltration of lymphocytes in the graft by day 2, and the architecture of the testis tissue was disrupted. The renal tissue also showed obvious lymphocytic infiltration adjacent to as well as within the graft. By day 7, there was little recognizable testis tissue and lymphocytic infiltrate was diminished, indicating that the destructive process had peaked before this time. These findings establish the role of the Fas ligand in immunosuppression, and show that the presence of a functional Fas ligand gene protects transplanted testicular tissue from graft rejection.

Example 8

Effect of Fas Ligand on Sertoli Cell Immunosuppressive Activity

To establish if isolated Sertoli cells could duplicate the results obtained with testis tissue grafts (Example 6), Sertoli cells were isolated and purified from testicular tissue of B6-Gld and B6 mice and transplanted as single cell suspensions under the kidney capsule in Balb/c mice, essentially as described by Selawry and Cameron (1993) Cell Transplantation 2:123 and Example 7 above. Testis were removed from mice and cut into small pieces in 5 ml HAM'S F12/DMEM media (Ham's media). The tissue was place in a 50 ml tube, 25 mls Ham's media added, and pelleted by centrifugation at 800×g for 2–5 min. The pellet was resuspended in 20 ml Ham's media containing 20 mg trypsin and 0.4 mg DNAse. The resulting mixture was placed in a 250 ml flask in a shaking water bath at 37° C. for 30 min. and pelleted at 800×g for 2–5 min. The cell pellet was resuspended at room temperature for 10 min in 20 ml of a solution containing 1M glycine, 2 mM EDTA, 0.01% soy bean trypsin inhibitor, and 0.4 mg DNAse. The mixture was centrifuged as above, and the cell pellet washed twice. Cells were resuspended in 20 ml Ham's media containing 10 mg collagenase, and placed in a shaking water bath at 37° C. for 5 minutes, pelleted, and resuspended in 20 ml Ham's media containing 20 mg collagenase and 0.1 mg DNAse. The sample was transferred to a 250 ml flask placed in a rocking water bath at 37° C. for 30 min. The cells were pelleted and washed as described above. Cells were resuspended in 10 ml Ham's media containing 20 mg hyaluronidase and 0.1 mg DNAse, and placed in 250 ml flask in a rocking water bath at 37° C. for 30 min. Cells were pelleted and washed. The final pellet was kept on ice until transplanted under the kidney capsule. The pellet may be clotted with blood drawn from the host mouse (see blood clot transplantation procedure described above).

Results identical to those described in Example 7 were obtained. B6-Gld Sertoli cells transplanted under the kidney capsule of histoincompatible Balb/c recipient mice remained intact. These results establish that the Fas ligand is an effective immunosuppressive factor responsible for the immunosuppressive effects of Sertoli cells.

Example 9

Diagnostic use of Fas Ligand Expression for Selecting Donor Tissue or Recipient Transplantation Site The discovery of the relationship between a functioning Fas ligand gene and protection from graft rejection may be applied diagnostically. The ability of various non-lymphoid tissue sources to express Fas ligand, detected either by examination of tissue with monoclonal antibodies to Fas ligand or by assessing Fas ligand mRNA by RT-PCR, allows prediction of the capacity for a specific tissue to be retained or rejected following transplantation. Tissues expressing a high level of Fas ligand provide a preferred site for successful organ engraftment. Screening donor tissue for Fas ligand expression will also aid in predicting transplantation success.

The invention is shown herein in what is considered to be the most practical and preferred embodiments. It is recognized, however, that departures may be made therefrom which are within the scope of the invention and that obvious modifications will occur to one skilled in the art upon reading this disclosure.

What is claimed is:

1. A method of suppressing T-lymphocyte-mediated graft rejection in a recipient mammal, said method comprising introducing into said mammal a cell which is transfected with a gene encoding a biologically-active form of Fas ligand, said cell expressing said Fas ligand, whereby rejection of the graft is suppressed.

2. The method of claim 1, wherein said cell is a cell of said graft.

3. The method of claim 1, wherein said cell is not a part of said graft.

4. The method of claim 1, wherein said cell is obtained from a transgenic mammal selected from the group consisting of a first transgenic mammal into which said gene has been introduced at an embryonic stage and a second transgenic mammal which is a descendent of said first transgenic mammal.

5. A method of suppressing T-lymphocyte-mediated islet cell graft rejection in a recipient mammal, said method comprising introducing into said mammal a cell which is transfected with and expresses a gene encoding a biologically-active form of Fas ligand, whereby rejection of the islet cell graft is suppressed.

6. A method for suppressing and preventing T-lymphocyte-mediated diabetic disease recurrence in a mammal, said method comprising introducing into said mammal an insulin-producing cell and a cell which is transfected with and expresses a gene encoding a biologically-active form of Fas ligand, whereby diabetic disease recurrence is suppressed or prevented.

7. A method for treating T-lymphocyte-mediated diabetic disease in a mammal, said method comprising introducing into said mammal a cell which is transfected with and expresses a gene encoding a biologically-active form of Fas ligand, whereby destruction of said mammal's islet cells is suppressed.

* * * * *

UNITED STATES PATENT AND TRADEMARK OFFICE
CERTIFICATE OF CORRECTION

PATENT NO. : 5,759,536
DATED : June 2, 1998
INVENTOR(S) : Bellgrau et al.

It is certified that error appears in the above-identified patent and that said Letters Patent is hereby corrected as shown below:

On the title page, item [54], and in column 1, line 1: Please delete "Surpress" and insert therefor --Suppress--.

Signed and Sealed this

Eighth Day of June, 1999

Attest:

Q. TODD DICKINSON

Attesting Officer

Acting Commissioner of Patents and Trademarks